United States Patent
Hawkins et al.

(10) Patent No.: US 9,271,711 B2
(45) Date of Patent: Mar. 1, 2016

(54) METHODS AND DEVICES FOR TISSUE RETRACTION

(75) Inventors: J. Riley Hawkins, Cumberland, RI (US); Christopher Ramsay, West Wareham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 185 days.

(21) Appl. No.: 13/435,373

(22) Filed: Mar. 30, 2012

(65) Prior Publication Data

US 2013/0261401 A1 Oct. 3, 2013

(51) Int. Cl.
| | |
|---|---|
| *A61B 1/32* | (2006.01) |
| *A61B 17/02* | (2006.01) |
| *A61B 17/00* | (2006.01) |
| *A61B 19/00* | (2006.01) |

(52) U.S. Cl.
CPC ........... *A61B 17/0206* (2013.01); *A61B 17/025* (2013.01); *A61B 17/0293* (2013.01); *A61B 2017/00477* (2013.01); *A61B 2017/0256* (2013.01); *A61B 2019/444* (2013.01); *A61B 2019/446* (2013.01)

(58) Field of Classification Search
CPC ... A61B 17/02; A61B 17/026; A61B 17/0293
USPC ................... 600/22–228, 231, 232
See application file for complete search history.

(56) References Cited

U.S. PATENT DOCUMENTS

| | | | | |
|---|---|---|---|---|
| 1,194,319 | A * | 8/1916 | Pretts et al. ................... | 600/224 |
| 1,706,500 | A * | 3/1929 | Smith ........................... | 600/232 |
| 3,054,398 | A | 9/1962 | Kobler | |
| 3,744,481 | A * | 7/1973 | McDonald .................... | 600/213 |
| 3,749,088 | A * | 7/1973 | Kohlmann ..................... | 600/215 |
| 3,998,217 | A * | 12/1976 | Trumbull et al. ............. | 600/233 |
| 4,165,746 | A * | 8/1979 | Burgin .......................... | 606/208 |
| 4,300,541 | A * | 11/1981 | Burgin .......................... | 600/213 |
| 5,297,538 | A * | 3/1994 | Daniel .......................... | 600/206 |
| 5,667,481 | A * | 9/1997 | Villalta et al. ................ | 600/224 |
| 5,865,731 | A * | 2/1999 | Lenox et al. .................. | 600/232 |
| 6,090,043 | A * | 7/2000 | Austin et al. .................. | 600/217 |
| 6,196,969 | B1 * | 3/2001 | Bester et al. .................. | 600/224 |
| 6,945,933 | B2 | 9/2005 | Branch et al. | |
| 7,473,222 | B2 * | 1/2009 | Dewey ............... | A61B 17/0206 600/210 |

(Continued)

FOREIGN PATENT DOCUMENTS

WO 2011/059498 A1 5/2011

OTHER PUBLICATIONS

U.S. Appl. No. 13/435,355 filed Mar. 30, 2012.

(Continued)

*Primary Examiner* — Jan Christopher Merene
*Assistant Examiner* — Atiya Mahmud
(74) *Attorney, Agent, or Firm* — Nutter McClennen & Fish LLP

(57) ABSTRACT

Methods and devices are provided for retracting tissue. In one exemplary embodiment, a retractor is provided that includes a base and a plurality of blades configured to removably and replaceably mate to the base. One or more of the plurality of blades can be configured to mate to the base in one of a plurality of available positions. In use, one or more adjustment mechanisms can be actuated to move one or more of the blades, thereby forming a pathway through tissue. The retractor can be formed from one or more radiolucent materials.

10 Claims, 13 Drawing Sheets

(56) References Cited

U.S. PATENT DOCUMENTS

| | | | |
|---|---|---|---|
| 7,537,565 B2* | 5/2009 | Bass | A61B 17/0206 600/219 |
| 7,594,888 B2 | 9/2009 | Raymond et al. | |
| 7,819,801 B2 | 10/2010 | Miles et al. | |
| 7,931,589 B2 | 4/2011 | Cohen et al. | |
| 7,935,053 B2 | 5/2011 | Karpowicz et al. | |
| 7,988,625 B2 | 8/2011 | Abdelgany et al. | |
| 8,038,611 B2 | 10/2011 | Raymond et al. | |
| 2005/0159650 A1* | 7/2005 | Raymond et al. | 600/201 |
| 2007/0083086 A1 | 4/2007 | LeVahn et al. | |
| 2007/0203399 A1* | 8/2007 | Gephart et al. | 600/219 |
| 2007/0208227 A1* | 9/2007 | Smith | A61B 1/313 600/219 |
| 2008/0183046 A1 | 7/2008 | Boucher et al. | |
| 2008/0214898 A1 | 9/2008 | Warren | |
| 2009/0036746 A1* | 2/2009 | Blackwell et al. | 600/219 |
| 2009/0306480 A1* | 12/2009 | Protopsaltis | 600/219 |
| 2010/0286486 A1 | 11/2010 | Parker et al. | |
| 2011/0098535 A1 | 4/2011 | Pimenta et al. | |
| 2011/0105850 A1 | 5/2011 | Voegele et al. | |
| 2011/0144687 A1 | 6/2011 | Kleiner | |
| 2011/0160585 A1 | 6/2011 | Akyuz et al. | |
| 2011/0245621 A1 | 10/2011 | Frasier et al. | |
| 2011/0301422 A1* | 12/2011 | Woolley et al. | 600/215 |
| 2011/0313256 A1 | 12/2011 | Raymond et al. | |
| 2012/0245432 A1* | 9/2012 | Karpowicz et al. | 600/224 |

OTHER PUBLICATIONS

International Search Report and Written Opinion for Application No. PCT/US2013/33873 mailed Jun. 12, 2013 (29 Pages).

* cited by examiner

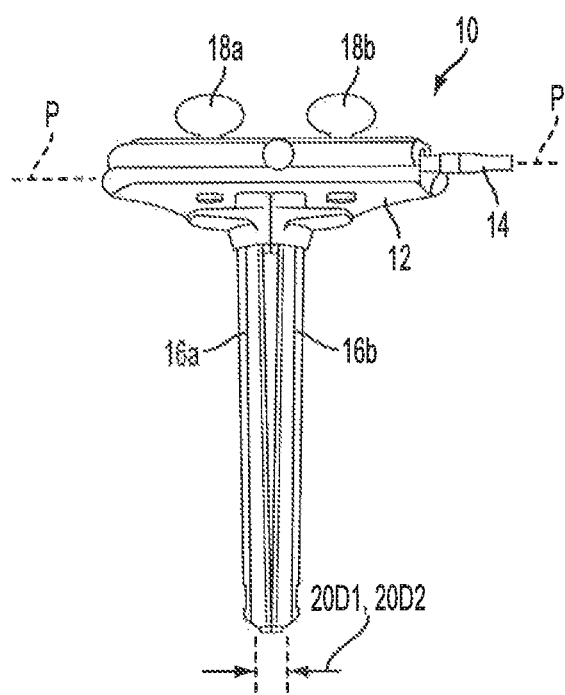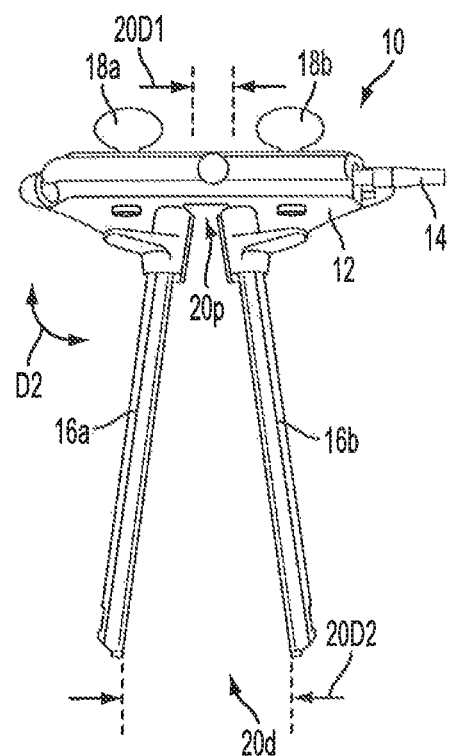

METHODS AND DEVICES FOR TISSUE RETRACTION

FIELD OF THE INVENTION

The present invention relates generally to methods and devices for tissue retraction, and in particular to bladed retractors and methods for use.

BACKGROUND OF THE INVENTION

In surgical procedures, it is preferable to minimize or reduce trauma to the patient and damage to tissue. To achieve this result, surgeons try to keep incisions as small as possible. However, it is usually necessary that the surgeon have a clear view of the operating field.

A variety of retractors are available to keep an incision open and provide a clear view of the operating field. Retractors are used in surgical operations to reposition muscular tissue, vessels, nerves, and other tissue with the aid of retractor blades, thereby providing access to the site of the operation. Surgical retractors are particularly important in performing surgical procedures that involve the spinal column, where access to the surgical site can be obtained, for example, through a posterior, posterior-lateral, anterior, lateral, or an anterior-lateral approach.

Retraction can be performed in a variety of ways. In some embodiments, a step-wise dilation of the surgical incision can be performed to gradually dilate the muscles and tissues to the required size to insert the retractor. Step-wise dilation can involve the use of a series of dilators or cannulae with successively larger diameters. This method involves first inserting the smallest dilator or cannula into an incision. Then a second dilator or cannula, with a slightly larger diameter, is slid over the smaller dilator or cannula and into the incision, thereby causing the incision to expand to the slightly larger diameter of the second dilator or cannula. This process can be repeated using a series of dilators or cannulae with successively larger diameters, until the incision is large enough to allow for insertion of the retractor. Once positioned, the retractors produce a small surgical site or window.

In some embodiments, a retractor can include multiple blades attached to a frame. The blades can be inserted into tissue and moved apart from one another to retract the tissue. However, moving the blades apart from one another can be cumbersome depending on where access to the surgical site is obtained, e.g., awkward positioning of the surgeon relative to the retractor during lateral approach to a spine. It can also be difficult to adjust the blades to a particular desired position without moving the blades apart from one another too much, thereby causing problem(s) such as harming nearby tissue or pushing against a nerve.

Accordingly, a need exists for improved methods and devices for tissue retraction.

SUMMARY OF THE INVENTION

In one embodiment, a surgical method for retracting tissue is provided that includes mating a first retractor blade in one of at least two positions to a base of a retractor, mating a second retractor blade in one of at least two positions to the base of the retractor, inserting the first and second retractor blades through an incision formed in tissue, and actuating at least one adjustment mechanism on the base to move the first and second retractor blades relative to one another to thereby expand the incision.

Prior to inserting, a third retractor blade can be mated to the base of the retractor, and the first, second, and third retractor blades can be inserted through the incision. Actuating at least one adjustment mechanism can include actuating a first adjustment mechanism to move the first and second retractor blades relative to one another, and actuating a second adjustment mechanism to move the third retractor blade relative to the first and second retractor blades. The first and second retractor blades can move simultaneously, and the third retractor blade can be movable independent of the first and second retractor blades. In one embodiment, the third retractor blade can be mated to the base by a snap-fit. In other aspects, the first and second retractor blades can mate to a distal surface of the base, and the third retractor blade can mate to a proximal surface of the base. Optionally, after expanding the incision, an area including the incision can be radioimaged to produce a radio image, the base and the retractor blades mated to the base being radiolucent such that the base and the retractor blades mated to the base are not visible in the radio image.

In some embodiments, the first retractor blade can be mated to the base in a first position. The first retractor blade can be detached, and the first retractor blade can be mated to the base in a second position offset from the first position.

The first, second, and third retractor blades can each have a variety of configurations. For example, each of the first and second retractor blades can be mated to the base by a compression fit, and/or each of the first and second retractor blades can have a corrugated cross-sectional shape. For another example, the first and second retractor blades can be mated to a distal-facing surface of the base.

In another aspect, a surgical retractor device is provided that includes a base and first, second, and third retractor blades. The distal portion of the first and second retractor blades each have a proximal portion removably and replaceably mateable to the base in at least two positions, and a distal portion configured to retract tissue. The third retractor blade has a proximal portion removably and replaceably mateable to the base, and a distal portion configured to retract tissue. The distal portions of the first, second, and third retractor blades define a pathway therethrough. The device can optionally include a first adjustment mechanism configured to adjust a position of the first and second retractor blades relative to one another, and a second adjustment mechanism configured to adjust a position of the third retractor blade relative to the first and second retractor blades.

The first, second, and third retractor blades can each have a variety of configurations. In some embodiments, the distal portions of the first and second retractor blades can include a longitudinally extending protrusion formed on an exterior surface thereof and a corresponding longitudinally extending channel formed on an interior surface thereof. The first, second, and third retractor blades can each mate to the base in any number of ways. For example, the first and second retractor blades can mate to the base solely by compression fit and/or the third retractor blade can mate to the base by a snap-fit. For another example, the first and second retractor blades can mate to a distal surface of the base, and the third retractor blade can mate to a proximal surface of the base.

In another embodiment, a surgical device is provided that includes a base having a central portion and first and second opposed arms extending therefrom, a first retractor blade removably and replaceably mated to the first arm of the base solely by compression fit, a second retractor blade removably and replaceably mated to the second arm of the base solely by compression fit, and a third retractor blade removably and replaceably mated to the central portion of the base. The third retractor blade has a proximal portion extending between the first and second arms of the base. In some embodiments, the device can include a first adjustment mechanism for simultaneously moving the first and second retractor blades relative to one another, and a second adjustment mechanism for moving the third retractor blade relative to the first and second retractor blades.

The first, second, and third retractor blades can each have a variety of configurations. For example, the third retractor blade can be mated to the base by a snap-fit. For another example, each of the first, second, and third retractor blades can have a channel extending longitudinally along an interior surface thereof such that an exterior surface thereof has a longitudinally extending protrusion extending therealong.

BRIEF DESCRIPTION OF THE DRAWINGS

The invention will be more fully understood from the following detailed description taken in conjunction with the accompanying drawings, in which:

FIG. 3 is a side view of one embodiment of a retractor in a closed position;

FIG. 4 is a side view of the retractor of FIG. 3 in an open position;

DETAILED DESCRIPTION OF THE INVENTION

Figure 1:
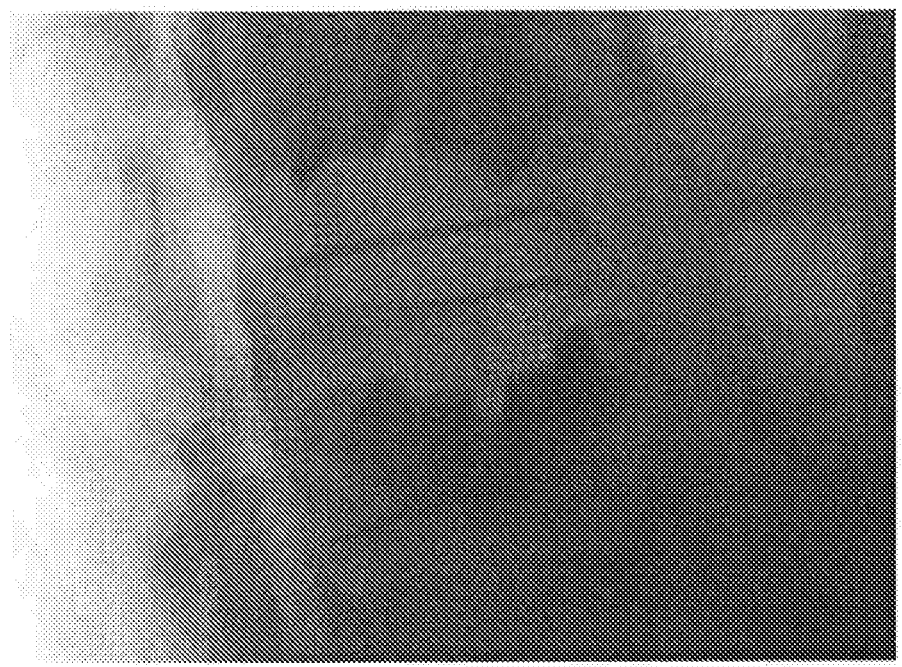
FIG. 1 is an x-ray image of one embodiment of a retractor at least partially formed from a radiolucent material retracting tissue adjacent to a spine.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for retracting tissue to form a pathway. In general, the methods and devices can allow multiple blades of a retractor to be selectively mated to a base of the retractor. In an exemplary embodiment, a retractor is provided that includes a base and a plurality of blades configured to removably and replaceably mate to the base. In one embodiment, one or more of the blades can be configured to mate to the base in one of a plurality of different positions. In other words, in a non-limiting example considering two blades matable to a base, a first blade can be configured to mate to the base in "M" different positions, and a second blade can be configured to mate to the base in "N" different positions, such that the first and second blades can be mated to the base in a total of (M×N) different combinations, where "M" and "N" represent positive integers greater than one, same or different from one another. In this way, blades each having a selected size, shape, and configuration can be mated to the base in selected positions in accordance with a specific patient and/or a specific surgical procedure in which the blades are to be used. Also, a retractor including removable blades can allow the base and/or the blades of the retractor to be more easily cleaned during and/or after use than a retractor including non-removable and non-replaceable blades because the blades can be removed from the base, thereby providing more complete access to the base and/or the blades. A retractor including removable blades can also allow at least the base of the retractor, which typically would not be inserted into a patient, to be re-used with the same or different blades in a same and/or subsequent surgical procedure in which the retractor is first used. Such reusability can save money and can save time during a surgical procedure.

In another exemplary embodiment, the retractor can be convertible and can include an optional blade that is configured to removably and replaceably mate to the base in a single available position. The optional blade can allow the retractor to be converted between a retractor having a first number of blades, e.g., two, to a retractor having a second, greater number of blades, e.g., three. In this way, the retractor can be selectively optimized for use with a specific patient and/or in a specific surgical procedure by configuring the retractor to have the first number of blades or have the second number of blades. The retractor can also include a first actuator coupled to the base and operatively connected to the one or more of the existing blades and a second actuator coupled to the base and operatively connected to the optional blade. The first actuator can be configured to be actuated to move the existing blades relative to the optional blade and/or to one another. The second actuator can be configured to move the optional blade relative to the existing blades. The first and second actuators can therefore allow the blades to retract tissue. The first and second actuators can also allow the existing blades to be moved separately from the optional blade, which can provide for greater granularity of control in retracting tissue.

In other aspects, a kit can be provided including a retractor base and a plurality of different retractor blades each configured to mate to the base in one or more predetermined positions, thereby providing for optimal selection of blades to mate to the base.

Figure 2:
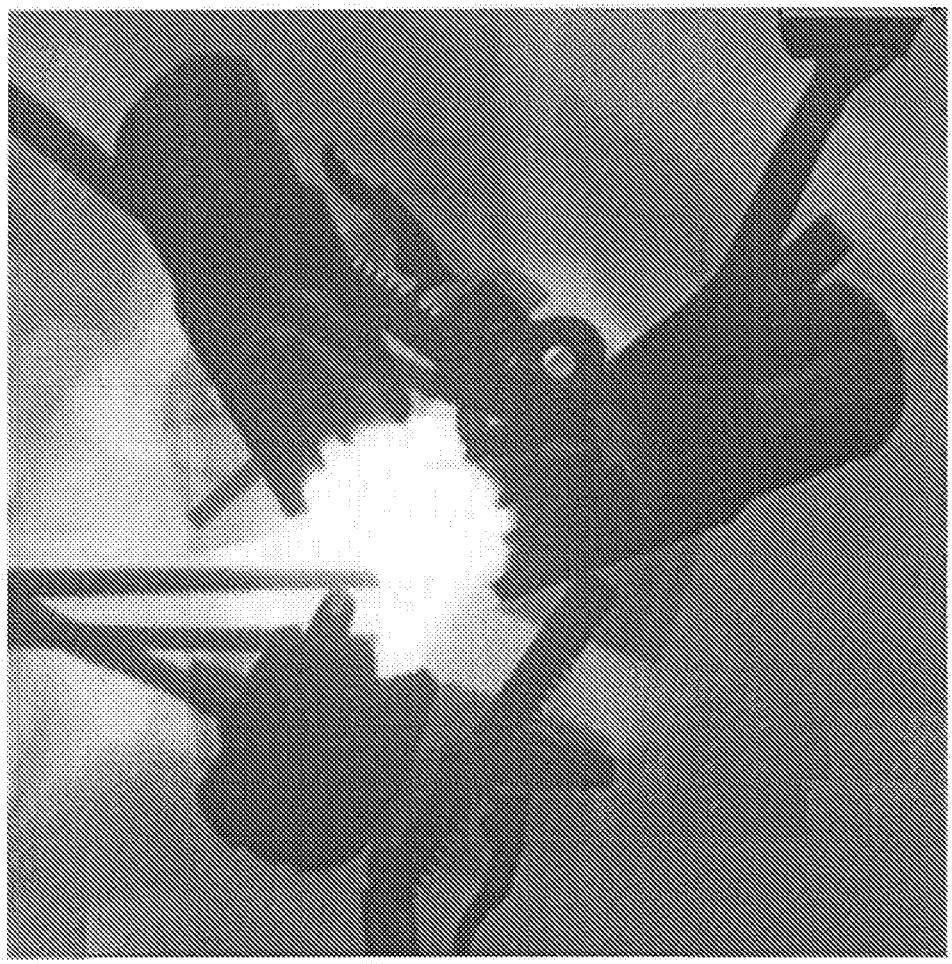
FIG. 2 is an x-ray image of one embodiment of a retractor formed from a non-radiolucent material retracting tissue adjacent to a spine.

The retractors disclosed herein can be formed from a variety of materials. Non-limiting examples of materials that can form a retractor include metals, polymers, and combinations thereof. Non-limiting examples of metals include titanium and stainless steel. Non-limiting examples of polymers include polyether ether ketone (PEEK), ultra-high-molecular-weight polyethylene (UHMPE), polyoxymethylene (POM) such as Delrin® available from DuPont of Wilmington, Del., Radel® polyphenylsulfone (Radel PPSU) available from Solvay S.A. of Ixelles, Brussels, Belgium, and carbon fiber reinforced polymers (CRFP) such as PEEK reinforced with carbon fibers. In an exemplary embodiment, the retractor can be formed from one or more radiolucent polymers, e.g., PEEK, which can allow the retractor to be substantially invisible in a radiographic image, e.g., an x-ray. A radiolucent retractor can facilitate inspection of a patient's anatomy and other objects in a radiographic image, e.g., without the retractor appearing dark on the image and hindering visualization of objects located behind the dark retractor and/or without reflections from blades of the retractor creating a bright spot within a working channel defined by the retractor blades and hindering visualization of objects located within or beyond a distal end of the working channel. FIG. 1 shows an example of an x-ray of a spine with a retractor that is retracting tissue adjacent the spine. The retractor in this illustrated embodiment includes a plurality of blades formed entirely from a radiolucent material(s) and a base having a majority thereof formed from a radiolucent material(s). The retractor of FIG. 1 is substantially invisible in the x-ray, which does not show a minority portion of the base formed from non-radiolucent material(s). In contrast, FIG. 2 (prior art) shows an example of an x-ray of a spine with a retractor that is not formed from radiolucent material(s) retracting tissue adjacent the spine. The retractor of FIG. 2 is plainly visible as a dark object in the x-ray.

Any portion of the retractor can be formed from a radiolucent material(s). At least a portion of the retractor within a zone of visualization can be formed from a radiolucent material(s), e.g., retractor blades and a portion of a retractor base to which the blades mate can be formed from a radiolucent material(s) so as to make the retractor blades and the portion of the retractor base substantially invisible in a radiographic image and help prevent bright radioimage glare within a working channel defined by the blades. In an exemplary embodiment, the entirety of the retractor blades and the entirety of connectors configured to connect the blades to the retractor base can be formed from a radiolucent material(s) so as to make the entire retractor blades and the entire connectors substantially invisible in a radiographic image. At least a portion of the base, e.g., a substantial portion thereof, can be formed from a radiolucent material(s). In some embodiments, the entire base can be formed from a radiolucent material(s). Elements, e.g., retractor blades and connectors, being entirely formed from a radiolucent material(s) also allows the elements to be 100% disposable. While it is desirable to have retractors formed from a radiolucent material(s), the use of such materials with surgical retractors can be difficult due to the use of numerous parts and moving parts. The retractors disclosed herein are particularly advantageous as they utilize a relatively small number of moving parts, thus allowing all or least a substantial portion thereof to be formed from a radiolucent material(s), e.g., the entireties of the blades and the connectors and a substantial portion of the base, while allowing integrity of the device to be maintained. In contrast, a retractor including a larger number of moving parts, such as conventional retractors, cannot be substantially formed from a radiolucent material(s) because the device would not be able to withstand the forces from the moving parts.

FIGS. 3-6 illustrate an exemplary embodiment of a retractor 10 configured to retract tissue. As shown, the retractor 10 can include a base 12 and a plurality of retractor blades 16a, 16b. Although the retractor 10 in this illustrated embodiment includes two blades, first blade 16a and second blade 16b, the retractor can include any number of blades, e.g., two, three, four, five, seven, etc. The retractor 10 can be configured to allow each of the blades 16a, 16b to be mated thereto in multiple different positions relative to the base 12, as discussed further below. The retractor 10 can also include at least one actuator or adjustment mechanism configured to move the blades 16a, 16b. In this embodiment, the retractor 10 includes a plurality of actuators. As shown, the retractor 10 includes first and second actuators 18a, 18b each configured to independently move the first and second blades 16a, 16b, respectively, relative to one another, and the retractor 10 includes a third actuator 14 configured to simultaneously move the blades 16a, 16b relative to one another.

Figure 5:
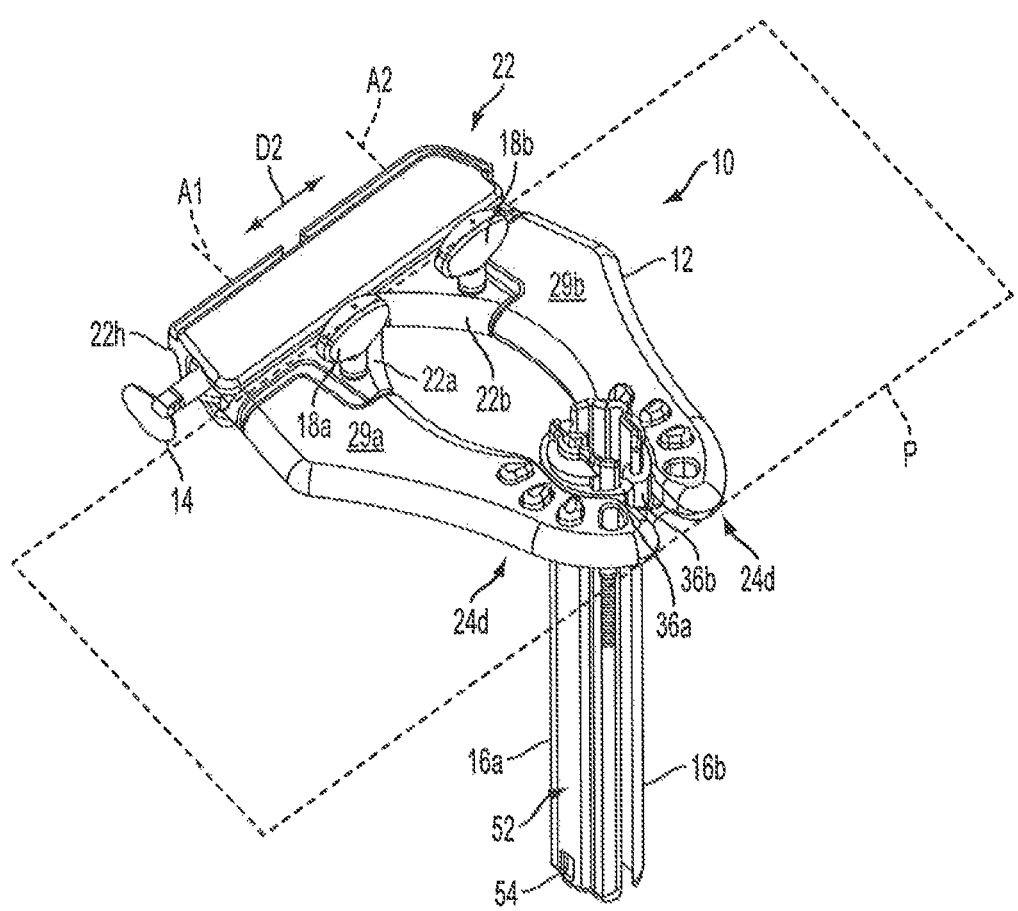
FIG. 5 is a top perspective view of the retractor of FIG. 3.
Figure 6:
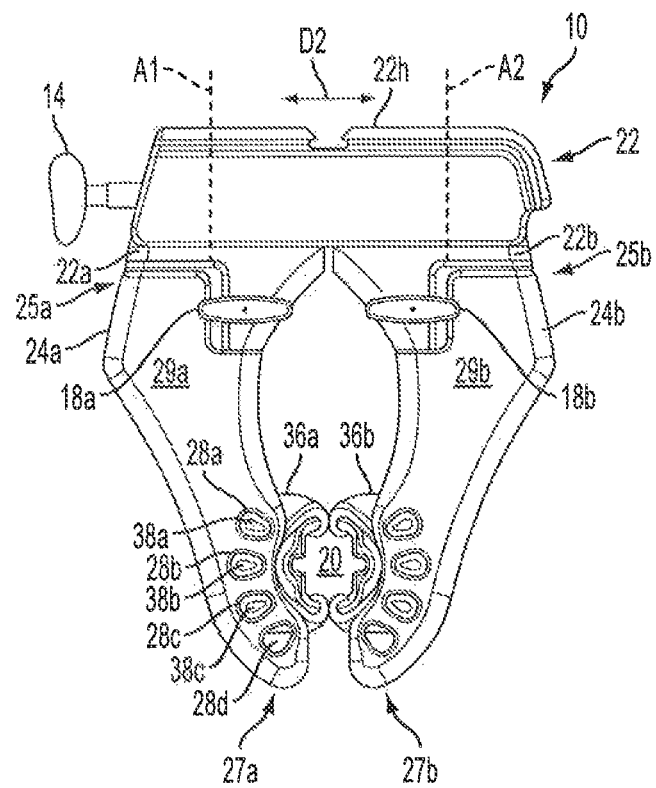
FIG. 6 is a top view of the retractor of FIG. 5.

The retractor 10 can be configured to be movable between a closed position, shown in FIGS. 3, 5, and 6, and an open position, shown in FIG. 4. As discussed further below, the third actuator 14 can be configured to move the retractor 10 between the open and closed positions. Generally, in the closed position, the blades 16a, 16b can be in a collapsed position in which they are at a first end of their full range of movement and are at a closest distance to one another. In this position, the blades 16a, 16b can define a working channel 20 having a diameter at its smallest size. Generally, in the open position, the retractor 10 can be in an expanded position in which the working channel 20 has a greater diameter than when the retractor 10 is in the closed position. When the retractor 10 is in the open or expanded position, the blades 16a, 16b can be fully open or partially open. In a fully open position, as shown in FIG. 4, the blades 16a, 16b are at a second end of their full range of movement in which they are at farther distance apart from one another and thereby define the diameter of the working channel 20 at its greatest size. In a partially open position, the blades 16a, 16b are at an intermediate position between the first and second ends of their full range of movement. The blades 16a, 16b can be positioned at any selected intermediate position between the closed and fully open positions. The distance between the blades 16a, 16b can therefore be increased or decreased to any desired extent, thereby allowing the retractor 10 to adjust to an almost infinite number of positions, which can allow the retractor 10 to be used with a variety of differently sized patients, with a variety of differently sized tissue, and with a variety of differently sized instruments inserted through the working channel 20.

Figure 7:
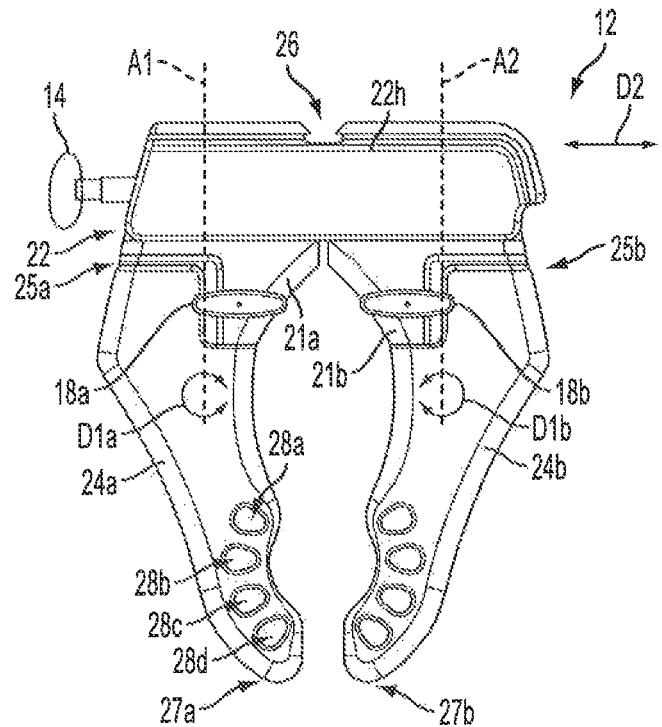
FIG. 7 is a top view of a base of the retractor of FIG. 5.

The base 12, which is illustrated as a standalone element in FIG. 7 with the actuators 14, 18a, 18b mated thereto, can have a variety of sizes, shapes, and configurations. The base 12 can include a central portion 22 and a plurality of mandibles or arms 24a, 24b extending therefrom. The central portion 22 of the base 12 can include the actuators 14, 18a, 18b coupled thereto. Generally, the actuators 14, 18a, 18b can be configured to move one or all of the arms 24a, 24b relative to the central portion 22 of the base 12 and hence also move one or all of the blades 16a, 16b relative to the central portion 22 of the base 12. The actuators 14, 18a, 18b are each discussed in further detail below.

The central portion 22 can have a variety of sizes, shapes, and configurations. As shown in FIGS. 5-7, the central portion 22 can generally have a substantially rectangular shape with opposed longitudinal sides and opposed, shorter latitudinal sides. The central portion 22 can also include flanges extending from one of the longitudinal sides thereof to which the first and second actuators 18a, 18b can be coupled, as also discussed further below. The central portion 22 can have a size that is large enough to facilitate manual handling and use of the retractor 10.

Figure 9:
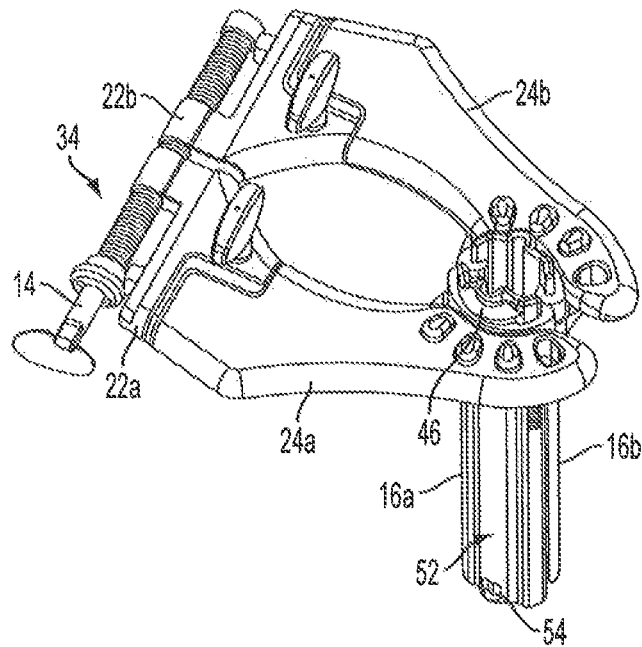
FIG. 9 is a top perspective view of the retractor of FIG. 5 with a handle portion of the retractor omitted.

The central portion 22 can include a handle portion 22h, a first support 22a, and a second support 22b. The handle portion 22h can obscure or cover portions of the supports 22a, 22b, as shown in FIGS. 5-7 and 9. The supports 22a, 22b can each include a threaded bore configured to threadably engage the third actuator 14, as shown in FIG. 9 and discussed further below. The first and second supports 22a, 22b can also be configured to seat the first and second actuators 18a, 18b, as also shown in FIG. 9 and discussed further below.

The handle portion 22h can be configured to be gripped by hand and/or be mounted to a stable object, e.g., a table, a wall, etc. Alternatively or in addition, the retractor 10 can include a flange (not shown) that extends radially outward from base 12, e.g., from the central portion 22 of the base 12, and that is configured to be gripped by hand and/or be mounted to a stable object. The handle portion 22h can include one or more mounting mechanisms configured to facilitate mounting of the retractor 10 to a stable object to allow hands-free use of the retractor 10 during a surgical procedure. In the illustrated embodiment, as shown in FIGS. 3-5 and 11, the handle portion 22h includes a notch 26 configured to be snap fit onto a complementary mounting mechanism (not shown), but the mounting mechanism can have a variety of other configurations, e.g., threads, clamp, etc. Although the mounting mechanism(s) can be formed anywhere in the base 12, as in the illustrated embodiment, the mounting mechanism(s) can be located on a first side of the central portion 22 of the base 12, e.g., a back side, opposite a second side of the central portion 22 of the base 12, e.g., a front side, from which the arms 24a, 24b extend, which can help prevent the stable object to which the mounting mechanism(s) mate(s) from interfering with movement of the blades 16a, 16b.

The base can include any number of the arms 24a, 24b, and the number of arms can equal a number of the blades 16a, 16b configured to be removably and replaceably mateable to the retractor 10 in various positions. Thus, although the illustrated retractor 10 includes first and second arms 24a, 24b, the retractor can include any number of arms, e.g., two, three, four, five, seven, etc. Alternatively, the retractor can include a number of arms less than a number of blades mateable thereto, such as when two or more blades can be simultaneously mated to a single arm. In the illustrated embodiment, only one of the blades 16a, 16b is mateable at a time to each arm, e.g., the first blade 16a to the first arm 24a and the second blade 16b to the second arm 24b or the second blade 16b to the first arm 24a and the first blade 16a to the second arm 24b. In another embodiment, one or more arms can be configured to simultaneously have two or more blades mated thereto.

The arms 24a, 24b can have a variety of sizes, shapes, and configurations. The arms 24a, 24b can have a claw shape such that they taper or curve inward toward the front ends 27a, 27b of the arms 24a, 24b, as shown in FIGS. 6 and 7. Such a taper or curve can allow the blades 16a, 16b mated to the arms 24a, 24b to be close together at least when the retractor 10 is in the closed position.

As mentioned above, the arms 24a, 24b can each extend from a same side of the central portion 22 of the base 12, and the arms 24a, 24b can be substantially co-planar with the central portion 22 of the base 12 at least when the arms 24a, 24b are not pivoted relative to the central portion 22, as discussed further below. In other words, the arms 24a, 24b can be configured to be located in a same plane P, shown in FIGS. 3 and 5, with respective proximal surfaces 29a, 29b and respective longitudinal axes A1, A2 of the arms 24a, 24b extending within the plane P, as shown in FIGS. 5-7. Back ends 25a, 25b of each of the arms 24a, 24b can be mated to the front side of the central portion 22 such that front ends 27a, 27b of the arms 24a, 24b are positioned a distance away from the central portion 22. The arms 24a, 24b are non-removably attached to the central portion 22 in the illustrated embodiment, which can help provide structural integrity to the base 12. In other embodiments, arms can be removably and replaceably attached to a central portion of a base, such as by threaded connection.

The arms 24a, 24b can be configured to move relative to another portion of the base 12, e.g., to the central portion 22, and to one another. The first and second actuators 18a, 18b can be configured to move the first and second arms 24a, 24b, respectively, as discussed further below. As in the illustrated embodiment, the arms 24a, 24b can each be configured to angle or pivot relative to the central portion 22 of the base 12 and relative to one another so as to adjust a distance between the front ends 27a, 27b thereof and to adjust diameter of the working channel 20. In other words, the first arm 24a can be configured to rotate about its longitudinal axis A1, as shown by directional arrow D1a in FIG. 7. Similarly, the second arm 24b can be configured to rotate about its longitudinal axis A2, as shown by directional arrow D1b in FIG. 7. Using the first arm 24a as an example for purposes of discussion, the movement of the first arm 24a can be angularly along direction D1a so as to change an angle of the blade 16a mated to the first arm 24a relative to the base 12 and to the other arm 24b and blade 16b mated thereto.

Angular positions of the first and second arms 24a, 24b, and the first and second blades 16a, 16b respectively mated thereto, can therefore be adjusted, which can facilitate adjustment of a diameter of the working channel 20 defined by the blades 16a, 16b. In other words, angling or pivoting one or both of the blades 16a, 16b toward one another can decrease the working channel's diameter, while angling one or both of the blades 16a, 16b away from one another can increase the working channel's diameter. Since the first and second arms 24a, 24b can be angled or pivoted independently, e.g., the first actuator 18b can be actuated independently from the first actuator 18a, the first and second arms 24a, 24b, the first and second blades 16a, 16b respectively mated thereto can be independently pivotably or angularly adjusted.

Each of the arms 24a, 24b can include a mating feature configured to mate to one of the blades 16a, 16b. The mating features can allow the first and second arm 24a, 24b to interchangeably mate to the first and second blades 16a, 16b, as discussed further below. If the retractor 10 is provided as part of a kit including one or more modular blades in addition to the modular first and second blades 16a, 16b, each of the blades can be configured to be interchangeably mated to the first and second arms 24a, 24b, which can facilitate speedy assembly of the retractor 10 and can simplify manufacturing of the blades 16a, 16b. Alternatively, the mating features of the first and second arms 24a, 24b can be keyed or otherwise uniquely configured differently from one another so as to be configured to mate with only a specific one of the first and second blades 24a, 24b.

The mating features of the arms 24a, 24b can have a variety of configurations. Non-limiting examples of mating features include threads, clamps, and clips. In the illustrated embodiment, the mating features include a plurality of openings formed through the arms 24a, 24b that are configured to mate the blades 16a, 16b to the base 12 by compression fit away from the central portion 22 and near the front ends 27a, 27b of the arms 24a, 24b, respectively. As discussed above, the arms 24a, 24b can be formed from a radiolucent material(s), e.g., polymer, in at least a portion of the arms 24a, 24b having the openings formed therethrough. This material can allow the blades 16a, 16b to mate to the base 12 solely by compression fit because the openings can provide adequate friction and expansion to securely, yet removably and replaceably, receive therein elements formed from a radiolucent material(s) to mate the blades 16a, 16b to the arms 24a, 24b, as discussed further below. For ease of discussion, the first arm 24a is discussed as a representative one of the arms 24a, 24b, and the first blade 16a is discussed as being mateable to the first arm 24a. A person skilled in the art will appreciate that the arms 24a, 24b may be substantially identical but not be precisely identical to one another due to one or more factors such as manufacturing tolerances, color coding and/or other coding such as printed numerical coding for ease of identification, etc.

As shown in FIGS. 6 and 7, the first arm 24a can include first, second, third, and fourth openings 28a, 28b, 28c, 28d, although the first arm 24a can include any number of openings, e.g., two or more. As discussed further below, a number of the openings 28a, 28b, 28c, 28d can define a number of different positions in which the first blade 16a can be mated to the first arm 24a. The openings 28a, 28b, 28c, 28d can each have a teardrop shape in the illustrated embodiment, but the openings 28a, 28b, 28c, 28d can each have any shape, e.g., circular, triangular, etc. By having an asymmetrical shape such as a teardrop, the openings 28a, 28b, 28c, 28d can define a direction that the first blade 16a should face when mated to the arm 24a, e.g., with an interior surface thereof facing the working channel 20. In an exemplary embodiment, each of the openings 28a, 28b, 28c, 28d can have a same shape as one another, which can facilitate mating of the first blade 16a thereto in a variety of possible positions relative to the base 12. Further, the openings in each of the arms 24a, 24b can have a same shape as one another, which can facilitate interchangeable mating of the first and second blades 16a, 16b to the first and second arms 24a, 24b. Although the openings 28a, 28b, 28c, 28d can be formed in any portion of the first arm 24a, as in the illustrated embodiment, the openings 28a, 28b, 28c, 28d can be formed in a front end of the first arm 24a, e.g., in an end opposite to an end of the arm mated to the central portion 22.

As mentioned above, the arms 24a, 24b can be configured to be movable relative to the central portion 22 of the base 12. The blades 16a, 16b mated to the arms 24a, 24b can therefore be moved with the arms 24a, 24b relative to the central portion 22 of the base 12. In other words, movement of the arms 24a, 24b can cause corresponding movement of the blades 16a, 16b mated thereto, thereby allowing tissue engaged by the blades 16a, 16b to be retracted.

As mentioned above, the first and second actuators 18a, 18b can be operatively connected to respective ones of the first and second blades 16a, 16b to cause movement thereof. The first and second actuators 18a, 18b can be operatively connected to their respective blades 16a, 16b in a variety of ways. As in the illustrated embodiment, the first and second actuators 18a, 18b can be configured to independently move respective ones of the first and second arms 24a, 24b, and hence respective ones of the first and second blades 16a, 16b, relative to one another. The first and second actuators 18a, 18b can each have a variety of configurations. In the illustrated embodiment, the first and second actuators 18a, 18b are configured the same as one another, but in other embodiments, the first and second actuators 18a, 18b can differ from one another. For ease of discussion, the first actuator 18a mated to the first arm 24a is discussed as a representative one of the first and second actuators 18a, 18b. A person skilled in the art will appreciate that the first and second actuators 18a, 18b may be substantially identical but not be precisely identical to one another due to one or more factors such as manufacturing tolerances, color coding and/or other coding such as printed numerical coding for ease of identification, etc.

Figure 8:
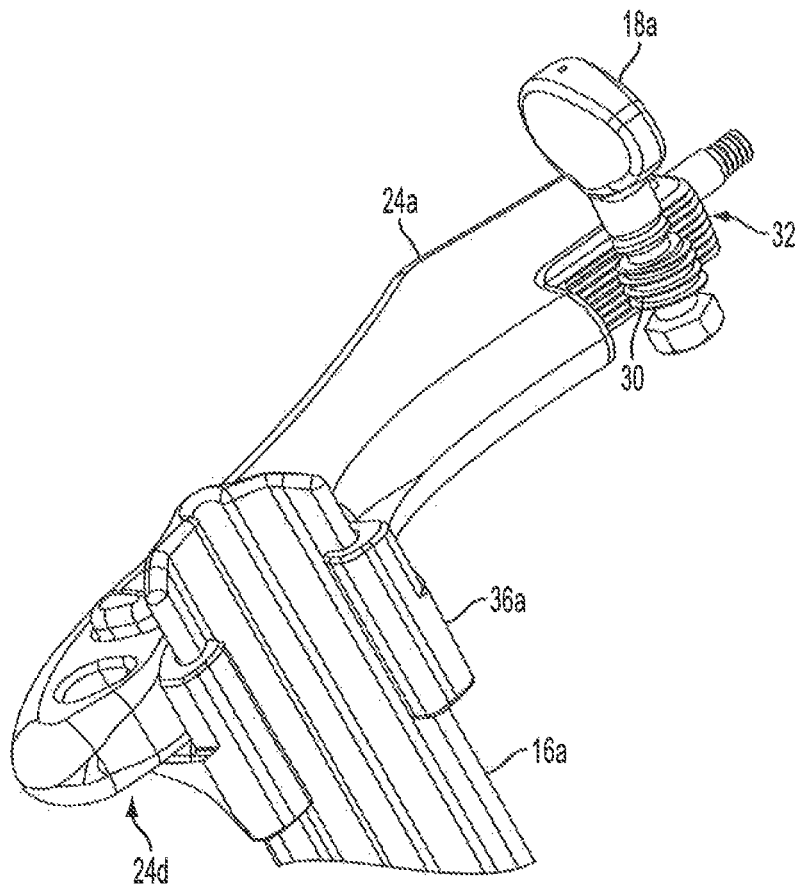
FIG. 8 is a side perspective, partial view of an arm of the retractor of FIG. 5 having a blade, a connector, and an actuator of the retractor mated thereto.

As shown in FIGS. 7 and 8, the first actuator 18a can include a threaded elongate shaft including threads 30 formed thereon configured to engage corresponding threads 32 formed on the first arm 24a. Although the first actuator 18a includes a threaded elongate shaft in this embodiment, the first actuator 18a can have other configurations, such as a lever, a push button, etc.

The first actuator 18a can be configured to be moved, e.g., rotated or turned, to threadably engage the threads 30 thereof with the first arm's threads 32, thereby causing movement of the first arm 24a, and the first blade 16a mated thereto, relative to the central portion 22 of the base 12 and relative to the other arm 24b. Depending on the direction of rotation or turning of the first actuator 18a, e.g., clockwise or counterclockwise, the first arm 24a can move clockwise or counterclockwise along the direction D1a. In other words, rotating the first and second actuators 18a, 18b can respectively cause the blades 16a, 16b to selectively pivot radially inward and radially outward. The pivoting of the blades 16a, 16b radially outward can cause the diameter of the working channel 20 to differ between a proximal end 20p and a distal end 20d thereof, as shown in FIG. 4, when the retractor 10 is in the open position, e.g., when the blades 16a, 16b are in the expanded position. In particular, a diameter 20D1 of the working channel 20 at the proximal end 20p thereof can be less than a diameter 20D2 of the working channel 20 at the distal end 20d thereof. The working channel 20 can thereof have a distally-tapering cone or pyramid shape when the retractor 10 is in the open position. In contrast, when the retractor 10 is in the closed position, e.g., when the blades 16a, 16b are in the collapsed position, as shown in FIG. 3, the diameters 20D1, 20D2 of the working channel 20 at the proximal and distal ends 20p, 20d can be substantially the same and can be substantially constant along a longitudinal length thereof.

As mentioned above, the third actuator 14 can be operatively connected to the first and second blades 16a, 16b to cause movement thereof. The third actuator 14 can extend longitudinally within the central portion 22 of the base 12, e.g., substantially parallel to the longitudinal sides of the central portion 22, and through one or both of the latitudinal sides of the central portion 22 to facilitate actuation of the third actuator 14.

The third actuator 14 can be operatively connected to their respective blades 16a, 16b in a variety of ways. As in the illustrated embodiment, the third actuator 14 can be configured to simultaneously move the first and second arms 24a, 24b, and hence simultaneously move the first and second blades 16a, 16b, relative to one another. The third actuator 14 can therefore be configured to be movable relative to the central portion 22 of the base 12 to cause the blades 16a, 16b to expand and collapse relative to the central portion 22 of the base 12 so as to increase and decrease the diameter of the working channel 20. Generally, the third actuator 14 can be actuated, e.g., rotated or turned, to cause the actuator 14 to move, e.g., rotate, relative to the central portion 22 of the base 12 and thereby cause the blades 16a, 16b to move relative to the central portion 22 of the base 12.

As shown in FIG. 9, the third actuator 14 can include a threaded elongate shaft including threads 34 formed thereon configured to engage corresponding threads (not shown) formed on the base 12, e.g., the central portion 22 of the base 12. The handle 22h of the central portion 22 is removed for clarity in FIG. 9. The third actuator 14 can be configured to be moved, e.g., rotated or turned, to threadably engage the threads 34 thereof with the base's threads, thereby causing movement of a core portion 22c of the central portion 22 and hence movement of the first and second arms 24a, 24b mated to the core portion 22c, as well as the first and second blades 16a, 16b respectively mated to the first and second arms 24, 24b. The third actuator 14 can therefore be configured to cause movement of the first and second arms 24a, 24b relative to one another and cause movement of the first and second blades 16a, 16b relative to one another. The movement of the first and second arms 24a, 24b, and hence the first and second blades 16a, 16b can be laterally along direction D2, as shown in FIGS. 5-7, in the plane P. The first and second arms 24a, 24b, and hence the first and second blades 16a, can therefore be configured to be separately movable angularly and rotationally, e.g., angularly via the first and second actuators 18a, 18b and rotationally via the third actuator 14. Although the third actuator 14 includes a threaded elongate shaft in this embodiment, the third actuator 14 can have other configurations, such as a lever, a push button, etc.

Depending on the direction of rotation or turning of the third actuator 14, e.g., clockwise or counterclockwise, the first and second arms 24a, 24b, and hence the first and second blades 16a, can move radially outward along the direction D2, e.g., away from a central longitudinal axis 20A of the working channel 20 to increase the diameter of the working channel 20 and move the retractor 10 to the open position with the blades 16a, 16b in the expanded position, or can move radially inward along the direction D2, e.g., toward the central longitudinal axis 20A to decrease the diameter of the working channel 20 and move the retractor 10 toward the closed position. In other words, rotating the third actuator 14 can cause the blades 16a, 16b to selectively move laterally, e.g., radially inward and radially outward, to selectively increase and decrease the diameter of the working channel 20.

Figure 10:
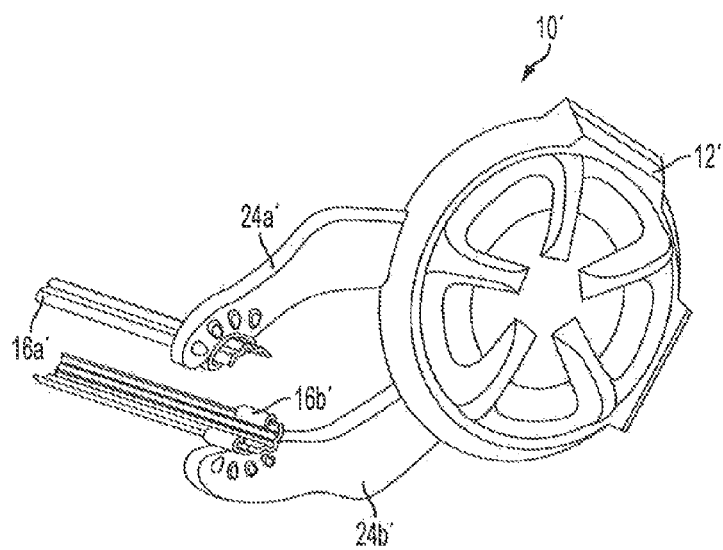
FIG. 10 is a perspective view of another embodiment of a retractor in an open position.
Figure 11:
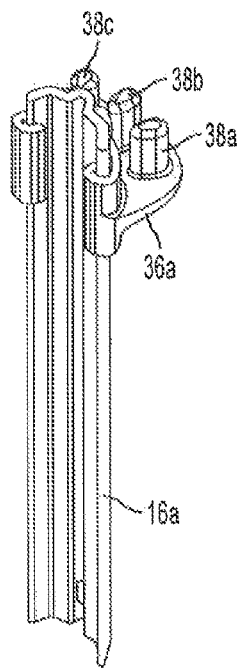
FIG. 11 is a side perspective view of the blade and the connector of FIG. 8.

FIG. 10 illustrates one embodiment of a retractor 10' including an actuator 14' operatively connected to first and second blades 16a', 16b' removably and replaceably mated to first and second arms 24a', 24b', respectively, extending from a base 12' to cause movement of the blades 16a', 16b'. The retractor 10' and its various elements, e.g., the first and second blades 16a', 16b', the base 12', etc., can be generally configured and used similar to other like-named elements discussed herein. In this embodiment, the actuator 14' can be configured to rotate to move the retractor 10' between the open and closed positions by moving the first and second blades 16a', 16b' toward and away from one another, thereby decreasing and increasing a size of a working channel defined by the blades 16a', 16b'. Although the retractor 10' includes only two removable and replaceable blades 16a', 16b', a retractor can, as mentioned above, include any number of removable and replaceable blades and any number of non-removable and non-replaceable blades. The actuator 14' can be configured to be seated in a track (not shown) formed in the base 12' and to be operatively connected to the blades 16a', 16b' to cause movement thereof relative to the base 12' when the actuator 14' is actuated, e.g., rotated within the track, relative to the base 12'. As in the illustrated embodiment, the actuator 14' can include a circular disc. In other embodiments, the actuator can include a ring having a central void and having a circular shape complementary to a circular track formed in a base.

As mentioned above, the actuator 14' can include a scroll gear or chuck, referred to herein as a "scroll gear," configured to operatively connect to the blades 16a', 16b' via interlocking features formed on the actuator 14' and on the blades 16a', 16b'. The scroll gear can have a variety of configurations and can be self-locking, as in the illustrated embodiment. In this way, the actuator 14' can be controllably rotated to any selected position relative to the base 12' to freely move the blades 16a', 16b' relative to the base 12' and hold the blades 16a', 16b' in any selected position relative to the base 12'. When the actuator 14' is not rotating, a thread (not shown) of the actuator 14', e.g., a pitch of the thread, can be configured to help hold the blades 16a', 16b' in position relative to the base 12', thereby preventing the blades 16a', 16b' from slipping relative to any tissue they are retracting and/or to any instrument inserted through the working channel defined by the blades 16a', 16b'. The pitch of the thread can be configured to counteract radially outward forces applied by the blades 16a', 16b' and thereby prevent teeth (not shown) of the blades 16a', 16b' engaging the thread of the actuator 14' from sliding relative to the thread when the actuator 14' is not being manually rotated. Exemplary embodiments of rotatable actuators such as the actuator 14' are described in further detailed in U.S. patent application Ser. No. 13/435,355 Entitled "Methods and Devices for Tissue Retraction" filed on Mar. 30, 2012, which is hereby incorporated by reference in its entirety.

Referring again to the retractor 10 of FIGS. 3-6, any one or more of the actuators 14, 18a, 18b can include one or more gripping features configured to facilitate manual movement thereof. Non-limiting examples of gripping features include a textured surface, one or more finger grips (e.g., proximally raised protrusions contoured on opposed sides thereof to receive fingertips), one or more finger or tool loops, one or more finger or tool depressions, a slide lever, a knob, a ridge, etc.

As will be appreciated by a person skilled in the art, each of the actuators 14, 18a, 18b can be manually actuated by hand and/or by using one or more tools. For non-limiting example, a tool can be pushed against an actuator to push or rotate the actuator and cause movement of the arm(s) operatively associated therewith. For another non-limiting example, any one or more of the actuators can include one or more tool openings or loops configured to receive an end of a tool therein such that moving the tool can push or rotate the actuator.

As mentioned above, although the retractor 10 in this embodiment includes a plurality of actuators 14, 18a, 18b, a retractor can include only one actuator. If a retractor only includes one actuator, in an exemplary embodiment, the retractor can include an actuator similar to the third actuator 14, e.g., an actuator configured to expand and collapse the retractor blades to adjust a size of the working channel defined by the blades.

The first and second blades 16a, 16b can be configured to mate to the first and second arms 24a, 24b in a variety of ways. In an exemplary embodiment, the first and second blades 16a, 16b can be configured to mate to a distal surface of the base 12, e.g., to distal surfaces 24d of the arms 24a, 24b of the base 12, as shown in FIGS. 5 and 8. The first and second blades 16a, 16b can be configured to directly mate to base 12, e.g., to be directly received in one or more of the openings formed in the arms 24a, 24b.

The blades 16a, 16b can have a variety of sizes, shapes, and configurations. In an exemplary embodiment, each of the blades 16a, 16b can include a proximal portion and a distal portion.

In the illustrated embodiment, the proximal portions of the first and second blades 16a, 16b can include first and second connectors 36a, 36b, respectively, as shown in FIGS. 5, 6, 8, 11, and 12. The first and second connectors 36a, 36b can be configured to respectively mate the first and second blades 16a, 16b to the base 12, e.g., the first and second arms 24a, 24b of the base 12, by being configured to be received within one or more of the openings formed in the arms 24a, 24b. In this way, the distal portions of the blades 16a, 16b can extend distally from the base 12. The connectors 36a, 36c can be configured to slidably engage the blades 16a, 16b to mate thereto, as discussed further below. The connectors 36a, 36b can be mated to the arms 24a, 24b in any order and can be mated to the arms 24a, 24b before or after the blades 16a, 16b are mated to the connectors 36a, 36b. The connectors 36a, 36b can facilitate interchangeability and cleaning of retractor blades by allowing slidable removal and replacement of blades therein. For ease of discussion, the first connector 36a mated to the first blade 16a and to the first arm 24a is discussed as a representative one of the first and second connectors 36a, 36b. A person skilled in the art will appreciate that the connectors 36a, 36b may be substantially identical but not be precisely identical to one another due to one or more factors such as manufacturing tolerances, color coding and/or other coding such as printed numerical coding for ease of identification, etc.

Figure 13:
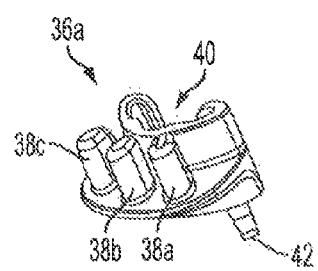
FIG. 13 is a side perspective view of the connector of FIG. 12.

The first connector 36a can include an internal track 40 configured to slidably engage the first blade 16a, as shown in FIG. 13. The internal track 40 can have a size and shape corresponding to a size and shape of the first blade 16a so as to securely engage the first blade 16a therein. Opposed ends of the internal track 40 can be rounded to facilitate sliding of the first blade 16a therein, as also shown in FIG. 13.

Figure 12:
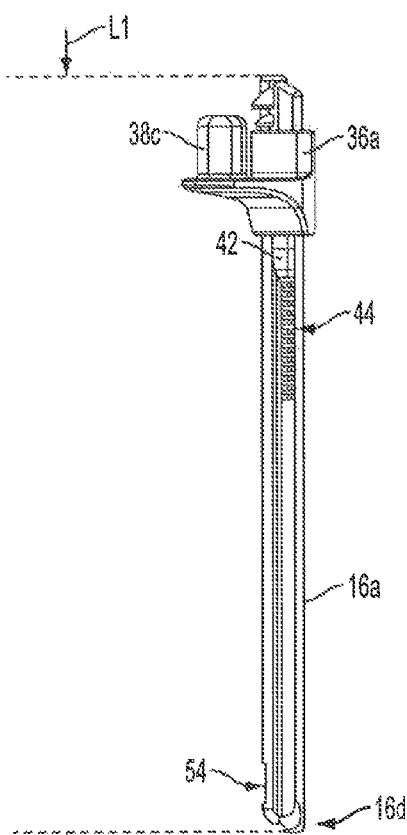
FIG. 12 is a side view of the blade and the connector of FIG. 10.

The first connector 36a can include a pawl or tooth 42 configured to engage a rack or teeth 44 formed on the first blade 16a, as shown in FIGS. 12 and 13. The tooth 42 of the first connector 36a can be configured to selectively engage different ones of the teeth 44 of the first blade 16a to lock the first blade 16a in position relative to the first connector 36a, e.g., prevent slidable motion of the first blade 16a through the internal track 40, absent application of an external force, e.g., a distally directed force on the first blade 16a. The first blade 16a can be configured to be advanced distal end 16d first into the internal track 40, with the tooth 42 engaging the blade's teeth 44 beginning at a distal-most one of the teeth 44, which can extend longitudinally along the first blade 16a. As the first blade 16a is advanced in a distal direction through the track 40, e.g., pushed distally by hand, the tooth 42 can move through the teeth 44. When the distal movement of the first blade 16a ceases, the engagement of the tooth 42 with the teeth 44 can lock the blade 16a in position relative to the connector 36a. The connector's tooth 42 and the blade's teeth 44 can have cooperating shapes to prevent the first blade 16a from moving in a proximal direction through the internal track 40. In this way, the blade 16a can be prevented from moving if the distal end 16d of the blade 16a abuts or pushes against tissue, bone, and/or other structure, thereby facilitating stable tissue retraction. The blade's teeth 44 can be formed nearer a proximal end 16p of the blade 16a than the distal end 16d of the blade 16a, thereby allowing most of the blade 16a to extend distally from the base 12, where it can be more effective to retract tissue. Conversely, the first blade 16a can be configured to be advanced proximal end 16p first into the internal track 40, with the tooth 42 engaging the blade's teeth 44 beginning at a proximal-most one of the teeth 44. The first blade 16a can be advanced through the track 40 similar to that discussed above, with the first blade 16a being configured to be advanced proximal end first into the track 40 and moved proximally, e.g., pulled in a proximal direction, to slide the blade 16a through the track 40.

The first connector 36a can include a plurality of pins or protrusions 38a, 38b, 38c configured to engage the openings 28a, 28b, 28c, 28d of the first arm 24a so as to be seated in selected ones of the openings 28a, 28b, 28c, 28d by compression fit. The protrusions 38a, 38b, 38c can therefore have a size and shape corresponding to a size and shape of the openings 28a, 28b, 28c, 28d, which as mentioned above, are teardrop-shaped in the illustrated embodiment. The first connector 36a can include a number of protrusions 38a, 38b, 38c that can be less than a number of the openings 28a, 28b, 28c, 28d. Although the first connector 36a includes three protrusions 38a, 38b, 38c in this embodiment, the first connector 36a can include one or more protrusions. In an exemplary embodiment, the number of protrusions can be at least one less than a number of the base openings in which the protrusion(s) can be seated. This configuration can allow the first blade 16a, to be mated to the first arm 24a in a plurality of different ways by being received in different combinations of the openings 28a, 28b, 28c, 28d. In other words, the first connector 36a can be mated to a subset of the openings 28a, 28b, 28c, 28d at any one time, with each different possible subset in which the first connector 36a can be mated defining a total number of possible ways in which the first connector 36a can be mated to the base 12.

In this embodiment, the first connector 36a can be mated to the first arm 24a in two different positions, one position with the protrusions 38a, 38b, 38c received in the first, second, and third openings 28a, 28b, 28c as shown in FIG. 6, and another position with the protrusions 38a, 38b, 38c received in the second, third, and fourth openings 28b, 28c, 28d. The second connector 36b can be similarly mated to the second arm 24b in two different positions, thereby resulting in a total number of four (2×2) different combinations in which the first and second blades 16a, 16b can be mated to the base 12. If, for non-limiting example, connectors matable to the first and second blades 16a, 16b each included two protrusions instead of three, the first and second blades 16a, 16b would be matable to the base 12 in nine (3×3) different combinations. If, for another non-limiting example, one of the connectors included three protrusions and the other included two protrusions, the first and second blades 16a, 16b would be matable to the base in six (2×3) different combinations.

In an exemplary embodiment, each of the blades 16a, 16b can be substantially the same as one another, as in the illustrated embodiment. A person skilled in the art will appreciate that the blades 16a, 16b may be substantially identical but not be precisely identical to one another due to one or more factors such as manufacturing tolerances, color coding and/or other coding such as printed numerical coding for ease of identification, etc. For ease of discussion, the first blade 16a, illustrated in FIGS. 9, 11, 12, 14, and 15, is discussed as a representative one of the blades 16a, 16b. Although the retractor 10 in this illustrated embodiment includes two blades 16a, 16b, a retractor can have any number of blades, and can, as discussed further below, be configured to include an optional additional blade.

Figure 15:
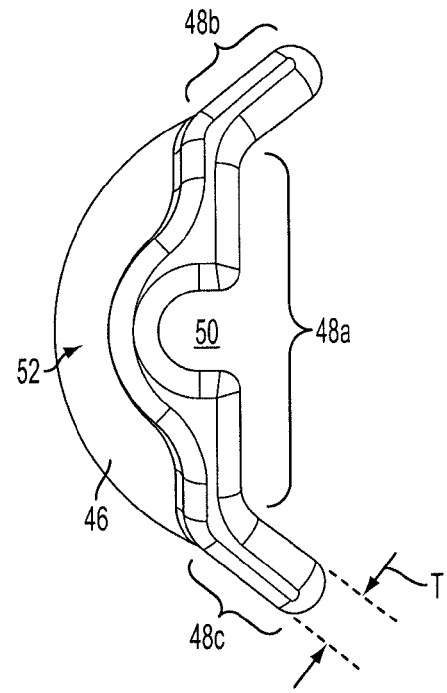
FIG. 15 is a top proximal view of the blade of FIG. 12.
Figure 16:
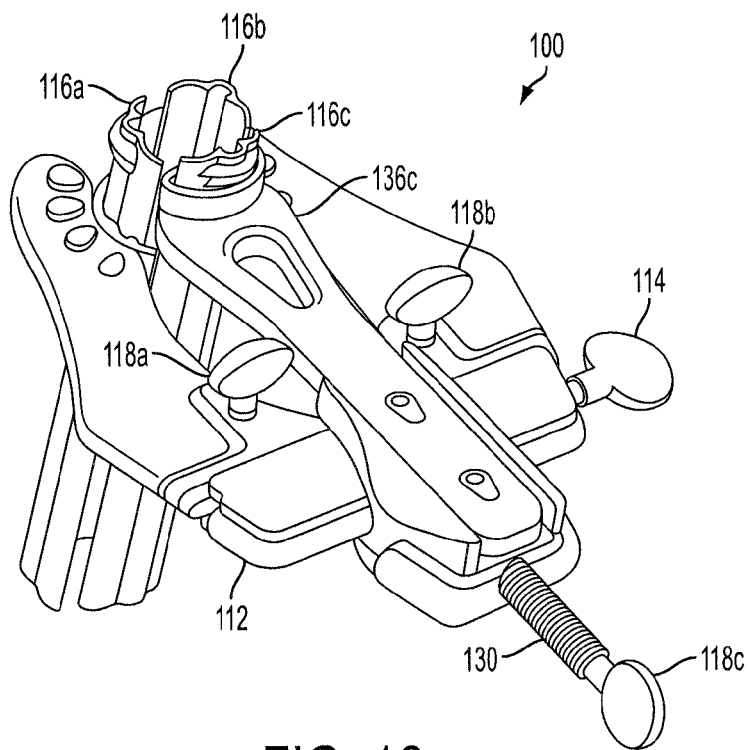
FIG. 16 is a top perspective view of another embodiment of a retractor in a closed position.
Figure 17:
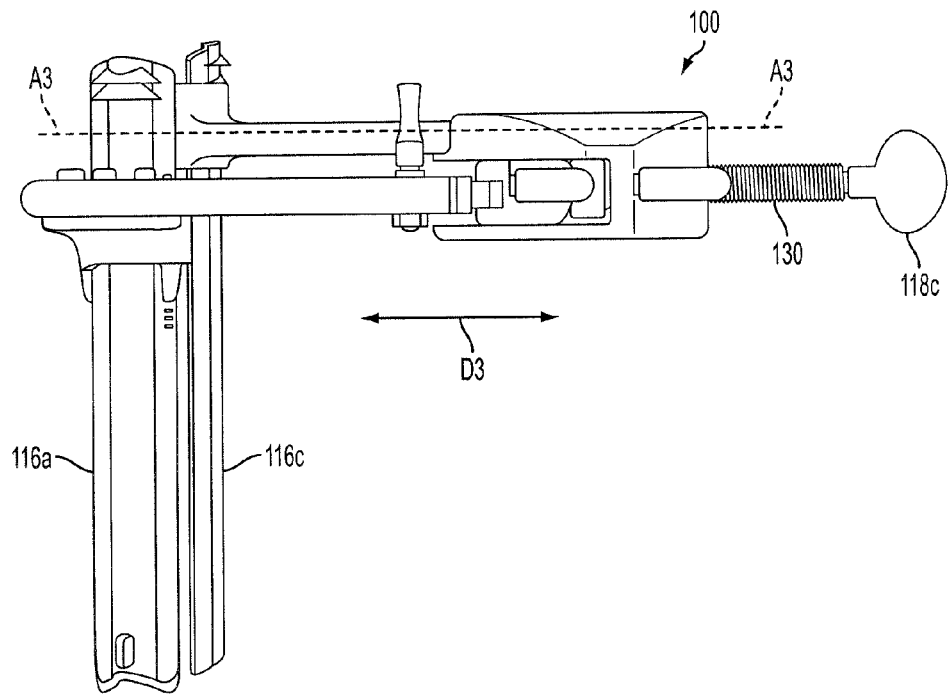
FIG. 17 is a side view of the retractor of FIG. 16.
Figure 18:
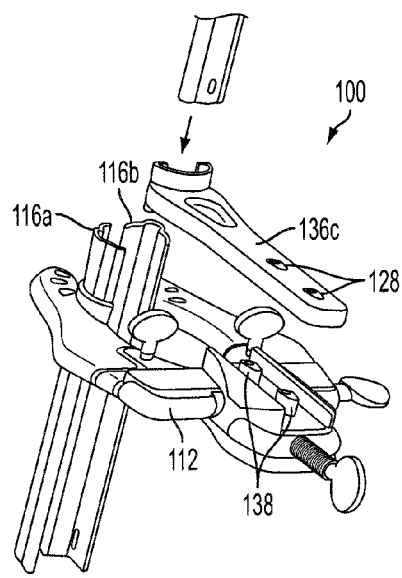
FIG. 18 is an exploded, partial view of the retractor of FIG. 16.

As shown in FIGS. 9 and 15, the first blade 16a can include at least one gripping feature 46 configured to help advance the first blade 16a through the track 40 of the connector 36a. In other words, the gripping feature 46 can be configured to facilitate manual movement of the first blade 16a. In this embodiment, the gripping feature 46 includes a single, crescent-shaped ridge extending radially outward, but the gripping feature can have other configurations, e.g., a textured surface, one or more finger grips, one or more finger or tool loops, one or more finger or tool depressions, a slide lever, a knob, a ridge, etc.

The first blade 16a can have any size and shape. In an exemplary embodiment, as shown in FIG. 12, the first blade 16a can have a linear profile, e.g., be linear in a longitudinal direction. The first blade 16a can have any longitudinal length L1, such as up to about 200 mm, e.g., in a range of about 80 to 150 mm. The first blade 16a and the connector 42, e.g., the blade's teeth 44 and the connector's tooth 42, can be configured to cooperate to allow a variable longitudinal length of the first blade 16a that is less than a complete longitudinal length L1 of the first blade 16a to extend distally beyond the distal surface 24d of the first arm 24a. In other words, a distal portion of the first blade 16a can extend distally beyond the distal surface 24d of the first arm 24a, and a proximal portion of the first blade 16a can extend proximally beyond the distal surface 24d of the first arm 24a. The distal portions of the first and second blades 16a, 16b can therefore define the working channel 20. A optional blade can therefore be configured to be adjustable to an optimal length in accordance with a specific patient and/or a specific surgical procedure in which the blade is to be used. In an exemplary embodiment, the first blade 16a can be configured to have a variable longitudinal length in a range of about 80 to 150 mm, e.g., in a range of about 120 to 150 mm, in a range of about 125 to 150 mm, in a range of about 80 to 120 mm, etc. In this illustrated embodiment, the first blade 16a has a fixed complete longitudinal length L1, but in another embodiment, the first blade's complete longitudinal length can be variable, such as by being configured as a telescoping blade. Additionally, a retractor can include blades that are all telescoping, or a retractor can include some telescoping blades and some non-telescoping blades. In some embodiments, a retractor can be configured to have one or more removable blade extenders mates to one or more blades of the retractor so as to extend the longitudinal lengths of the one or more blades.

Figure 14:
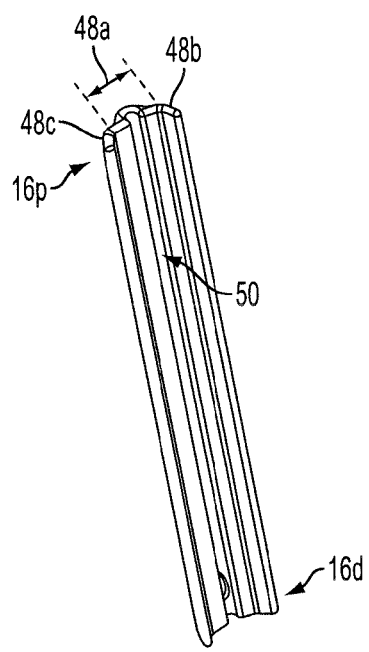
FIG. 14 is a side perspective view of the blade of FIG. 12.

The first blade 16a can have any thickness T, as shown in FIG. 15. In an exemplary embodiment, the blade thickness T can be relatively thin, e.g., about 2 mm. The first blade 16a can have a non-linear cross-sectional shape, as shown in FIGS. 14 and 15, which can help provide stiffness and strength to the relatively thin blade 16a.

The non-linear cross-sectional shape of the first blade 16a can vary. In this embodiment, the first blade 16a has a "tin roof" or corrugated cross-sectional shape having a mid-portion 48a with sloped portions 48b, 48c extending from each end of the linear mid-portion 48a. As shown in FIGS. 5, 9, 14, and 15, the mid-portion 48a can be linear on an interior surface of the blade, and the mid-portion can have an indentation therein that, along the longitudinal length L1 of the first blade 16a, can define a longitudinally extending channel 50 formed on the interior surface of the first blade 16a, e.g., facing the working channel 20, and a corresponding longitudinally extending protrusion 52 formed on an exterior surface of the first blade 16a. A retractor blade can include such a longitudinally extending channel and such a longitudinally extending protrusion regardless of the blade's cross-sectional shape. The channel 50 can have any size and shape, such as half-cylindrical as in this embodiment. The protrusion 52 can have also have any size and shape, corresponding to the size and shape of the channel 50. The channel 50 can be configured to receive a surgical instrument slidably inserted therethrough without obstructing a central portion of the working channel 20 defined by the blades 16a, 16b such that a second surgical instrument can be simultaneously inserted through the central portion of the working channel 20. Similarly, the channel 50 can be configured as a guide or track configured to slidably receive a corresponding rail coupled to a surgical instrument inserted through the working channel 20 so as to controllably allow advancement of the surgical instrument through the working channel 20. Non-limiting examples of surgical instruments that can be slidably received in the channel 50 include an endoscope, a fixation pin, and a nuero probe. In an exemplary embodiment, the channel 50 can be configured to seat a light source, e.g., a fiber optic cable, configured to direct light from adjacent the distal end 16d of the first blade 16a, thereby facilitating visualization of a surgical space. The light source can be fixedly secured within the channel 50, or the light source can be movably seated therein.

The first blade 16a can include a window 54 formed adjacent the distal end 16d of the first blade 16a, as shown in FIGS. 5 and 9. Although the first blade 16a includes only one window 54, a blade can include any number of windows. The window 54 can have any size and shape, e.g., a half-ellipse shape as shown in FIGS. 5 and 9, circular, square, triangular, etc. The window 54 can include open space, as in the illustrated embodiment. Providing an open window can facilitate heat transfer therethrough, e.g., if a heating element is advanced through the channel 50 and directs heat through the window. Alternatively, the window 54 can be at least partially covered, e.g., with a transparent film, which can allow light to pass therethrough and help prevent matter such as fluid and tissue from passing through the window 54. The window 54 can be configured to facilitate neuromonitoring, such as by allowing an electrode to pass therethrough or by having an electrode built therein with exposed metal that can extend longitudinally along the blade 16a, e.g., within the channel 50.

As mentioned above, a retractor can include another modular blade in addition to the plurality of modular blades discussed above, e.g., the first and second blades 16a, 16b. In this way, the retractor can be configured as a convertible retractor able to be effectively used with a first number of blades or with a second number of blades. In an exemplary embodiment, the retractor can be configured to include two modular blades each matable to a base of the retractor in a plurality of selectable positions and to allow selective mating of a third modular blade thereto. The retractor can therefore be configured for use without serial dilation, e.g., preferably as a two-bladed retractor, and for use with serial dilation, e.g., preferably as a three-bladed retractor. The additional modular blade can be configured to mate to the base in a single position, which can provide for predictable placement of the additional blade relative to the plurality of modular blades mated to the base.

FIGS. 16-22 illustrate an exemplary embodiment of a retractor 100 configured to retract tissue and configured to include a plurality of blades 116a, 116b and an optional additional blade 116c mated thereto. The retractor 100 and its various elements, e.g., the plurality of blades 116a, 116b; a base 112; actuators 114, 118a, 118b; etc., can be generally configured and used similar to other like-named elements discussed herein. The additional blade 116c can generally configured and used similar to the plurality of blades 116a, 116b, but the additional blade 116c can be configured to mate to the base 112 on a different surface of the base 112 than the plurality of blades 116a, 116b, which as discussed above can be mated to a distal-facing surface of the base 112. The additional blade 112c can be configured to mate to the base 112 in a single position, as in this illustrated embodiment, but an additional blade can be configured to mate to a base of a retractor in a plurality of positions similar to that discussed above regarding the blades 16a, 16b. The additional blade 116c can include an additional connector 136c in a proximal portion thereof that can be configured to facilitate mating of the additional blade 116c to the base 112. The retractor 100 can also include a fourth actuator 118c configured to independently move the additional blade 116c relative to the other blades 116a, 116b.

The additional connector 136c can be configured to slidably engage the additional blade 116c to mate thereto, similar to that discussed above regarding the connectors 36a, 36b. The additional connector 136c can be configured to mate the additional blade 116c to the base 112, by being configured to be secured to the base 112 in a single predetermined orientation. Although, as mentioned above, in another embodiment, an additional blade can be configured to mate to a base in a variety of different positions. The additional connector 136c can be configured to be secured to the base 112 in a variety of ways, e.g., threaded connection, clip, clamp, etc. In the illustrated embodiment, the additional connector 136c can be configured to be secured to the base 112 by a snap-fit, which can facilitate quick, easy assembly of the retractor 100. In another embodiment, an additional blade can be configured to mate to a base in another way, e.g., by a compression fit.

The additional connector 136c can include one or more openings 128 formed therein, similar to the openings 28a, 28b, 28c, 28d of the first arm 24a of the retractor 10. The one or more openings 128 can be configured to engage by snap-fit one or more corresponding pins or protrusions 138 extending from the base 112, e.g., from a proximal-facing surface of the base 112. The protrusion(s) 138 can therefore have a size and shape corresponding to a size and shape of the opening(s) 128, which similar to that mentioned above, can have any size and shape, e.g., teardrop-shaped. The connector 136c can include any number of openings 128, and the base 112 can include any number of protrusions 138. To facilitate mating of the additional blade 116c to the base 112 in a single predetermined orientation, the number of openings 128 can equal the number of protrusions 138 such that each of the openings 128 has a protrusion 138 received therein when the additional blade 116c is mated thereto. Conversely, similar to the blades 16a, 16b discussed above, when the plurality of modular blades 116a, 116b are mated to the base 112, at least one of the openings formed in each of the arms 124a, 124b can be empty, e.g., void of connector protrusions, when the blades 116a, 116b are mated to the base 112 by compression fit. Also similar to that discussed above, the additional blade 116c can be configured to directly mate to the base 112 rather than having an intervening connector 136c. To facilitate the snap-fit of the additional blade 116c to the base 112, the protrusion(s) 138 can be formed from a metal and the additional connector 136c can be formed from a radiolucent material(s).

The additional connector 136c being formed from a radiolucent material(s), e.g., polymer, in at least a portion of the additional connector 136c having the openings formed therethrough can allow the additional blade 116c to mate to the base 112 solely by a snap-fit because the openings can provide adequate friction and expansion to securely, yet removably and replaceably, mate the additional blade 116c to the base 112.

The fourth actuator 118c can be operatively connected to respective the additional blade 116c to cause movement thereof. The fourth actuator 118c can be operatively connected to the additional blade 116c in a variety of ways. As shown, the fourth actuator 118c can include a threaded elongate shaft including threads 130 formed thereon configured to engage corresponding threads (not shown) formed on the base 112. The fourth actuator 118c can be configured to be moved, e.g., rotated or turned, to threadably engage the threads 130 thereof with the base's threads, thereby causing movement of the additional connector 136c, and the additional blade 116c mated thereto relative to the other blades 116a, 116b. The movement of additional blade 116c can be linearly in a direction D3 along a longitudinal axis A3 of the proximal portion of the additional blade 116c, shown in FIG. 17, so as to change a distance between the additional blade 116c relative to the other blades 116a, 116b mated to the base 112. Depending on the direction of rotation or turning of the fourth actuator 118c, e.g., clockwise or counterclockwise, the additional blade 116c can move forward or backward along the longitudinal axis A3. Although the fourth actuator 118c includes a threaded elongate shaft in this embodiment, the fourth actuator 118c can have other configurations, such as a lever, a push button, etc.

Figure 19:
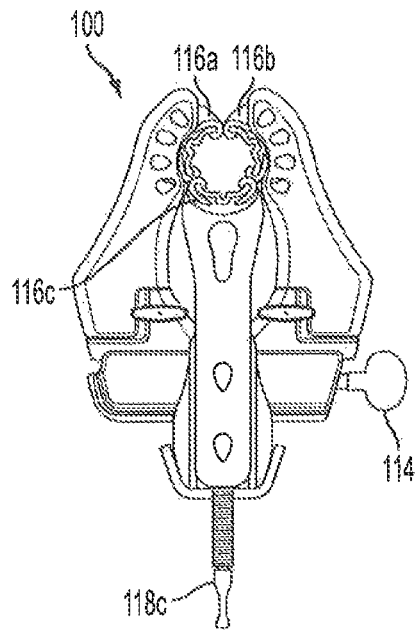
FIG. 19 is a top view of the retractor of FIG. 16.
Figure 20:
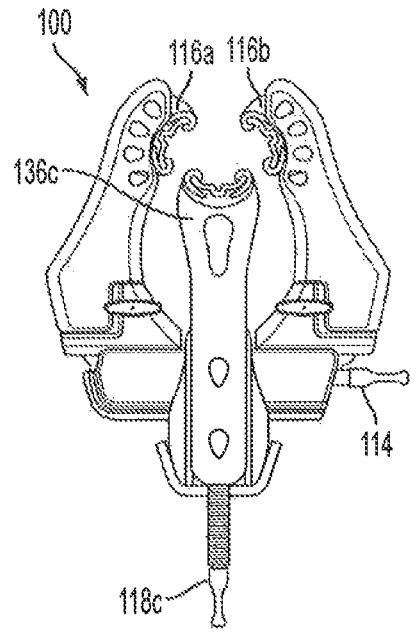
FIG. 20 is a top view of the retractor of FIG. 19 moved from the closed position to an open position.
Figure 21:
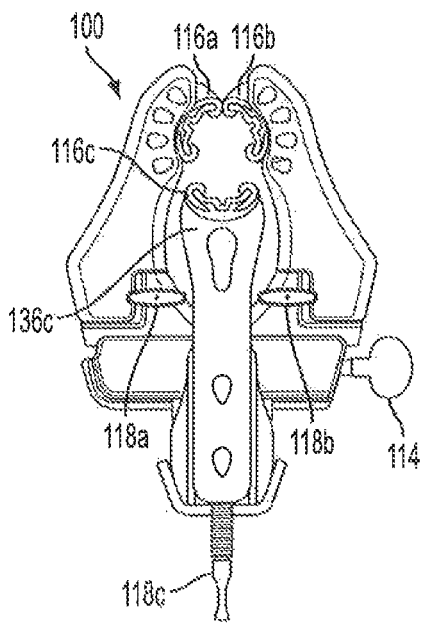
FIG. 21 is another top view of the retractor of FIG. 19 moved from the closed position to a second open position.
Figure 22:
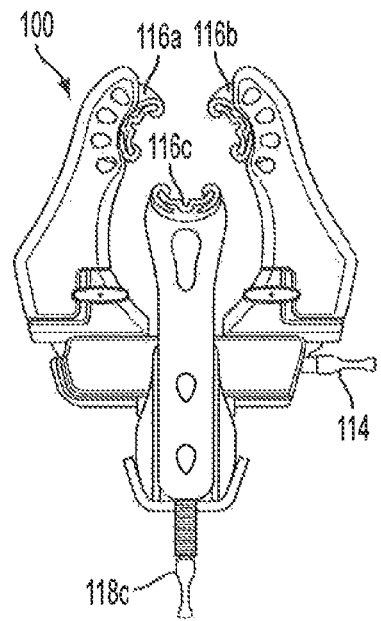
FIG. 22 is a top view of the retractor of FIG. 21 moved from the second open position to a third open position.

FIGS. 19-22 illustrate various relative movements of the blades 116a, 116b, 116c caused by various actuations of the actuators 114, 118a, 118b, 118c. FIG. 19 shows the retractor 100 in a closed position. FIG. 20 illustrates the retractor 100 moved from the closed position of FIG. 19 to an open position in response to actuation of the third actuator 114, which can cause the first and second blades 116a, 116b to move laterally, e.g., away from one another. Actuating the third actuator 114 can result in no movement of the additional blade 116c, as shown. FIG. 21 illustrates the retractor 100 moved from the closed position of FIG. 19 to an open position in response to actuation of each of the first and second actuators 118a, 118b, which can respectively cause the first and second blades 116a, 116b to angularly adjust, e.g., angle toward one another as shown in FIG. 21. Actuating one or both of the first and second actuators 118a, 118b can result in no movement of the additional blade 116c, as shown. FIG. 22 illustrates the retractor 100 moved from the open position of FIG. 21 to another open position in response to actuation of the third actuator 114, which can cause the first and second blades 116a, 116b to move laterally, e.g., away from one another. By providing actuators 114, 118a, 118b, 118c each configured to move at least one of the blades 116a, 116b, 116c without moving at least one of the other blades 116a, 116b, 116c, the retractor 100 can allow for greater granularity of control in retracting tissue and in sizing the working channel.

Figure 23:
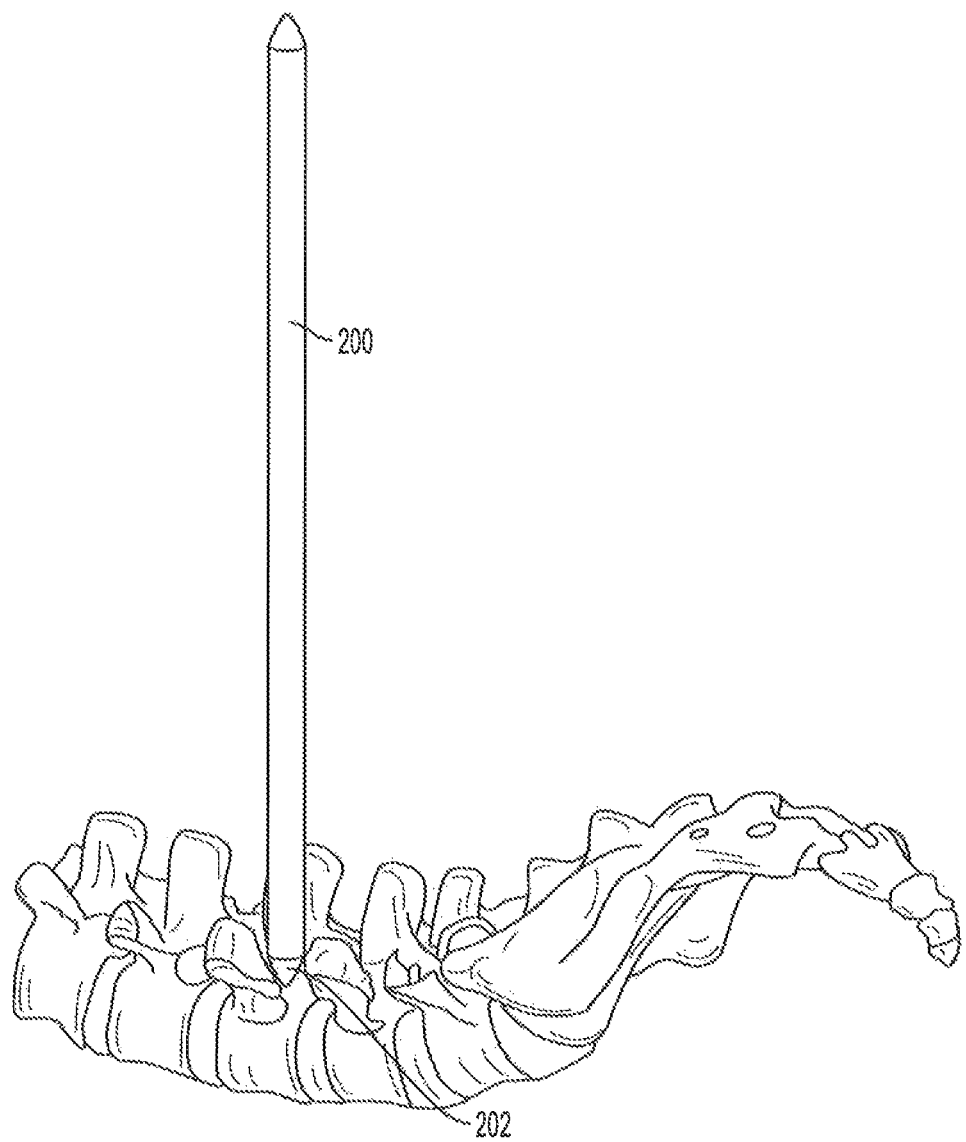
FIG. 23 is a perspective view of an obturator advanced to a spine.
Figure 24:
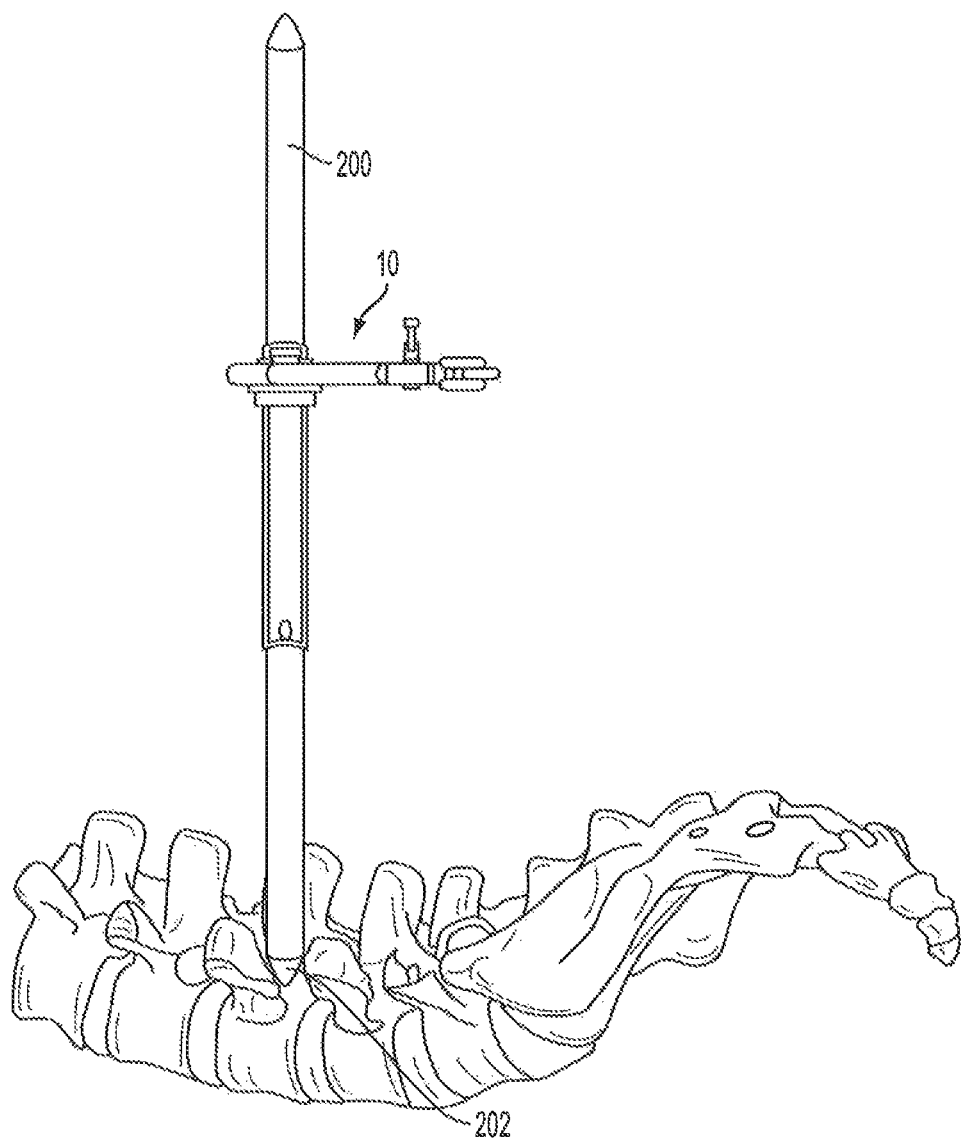
FIG. 24 is a perspective view of the retractor of FIG. 3 being advanced over the obturator of FIG. 23.
Figure 25:
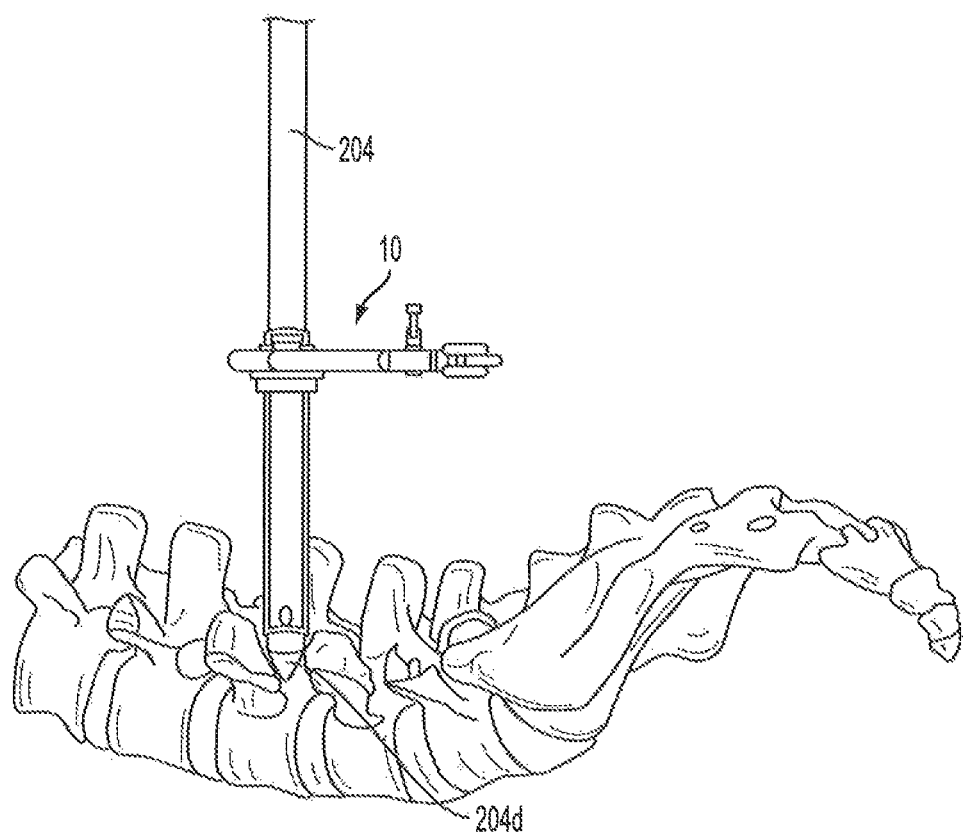
FIG. 25 is a perspective view of the retractor of FIG. 24 advanced to the spine and having a surgical instrument inserted therethrough.

In some embodiments, a retractor can be inserted over an obturator during insertion of the retractor to the depth of the surgical site or near the depth of the surgical site to be formed. FIGS. 23-25 illustrate one embodiment of such a method used to retract tissue near the spine of a human. Soft tissue and some bone mass has been omitted from the figures for clarity. A person skilled in the art will appreciate that while use of the retractor 10 of FIGS. 3-6 is shown and described with reference to FIGS. 23-25 as retracting tissue adjacent a spine, any retractor disclosed herein can be used similarly, and the methods and devices disclosed herein can be used to retract tissue in a variety of medical procedures at various places around a patient's body.

FIG. 23 illustrates an obturator 200 after it has been inserted into an incision and directed to a surgical site 202, e.g., next to a spinal column. Optionally, the obturator 100 can be directed along a guide wire (not shown) which has previously been tethered to the surgical site 202. Once the obturator 200 is in position at the surgical site 202, the retractor 10 can be advanced over the obturator 200, e.g., with the obturator passing through the working channel 20, to the surgical site 202. The retractor 10 in the closed position can be advanced alone over the obturator 200, as shown in FIG. 23. Alternatively, as will be appreciated by a person skilled in the art, the retractor 10 can be coupled to an introducer device (not shown) configured to advance the retractor 10 along the obturator 200. Whether advanced using an introducer device or not, the retractor 10 can be advanced distally to the surgical site 202 by pushing the retractor 10 down the length of obturator 200 to the surgical site 202, as shown in FIG. 24. Once the retractor 10 is at the surgical site 202, the obturator 200 can be removed from the incision, leaving the retractor 10 at the surgical site 202. Instead of using the obturator 200 to guide the retractor 10 to the surgical site 202, as will be appreciated by a person skilled in the art the retractor 10 can be advanced to the surgical site 202 in a number of other ways, e.g., using a guide wire, using an introducer device, hand insertion, etc. Optionally, at any point during the procedure, the retractor 10 can be attached to a surgical retractor positioning mechanism, e.g. a table, one or more a rigid arms, a wall, etc., to rigidly secure the retractor 10 at a fixed location relative to the surgical site 202.

Once positioned at the surgical site 202, the retractor 10 can be actuated as discussed above to retract tissue at the surgical site 202. With the retractor 10 in the closed position or in the open position, one or more surgical instruments 204 can be inserted through the working channel 20 of the retractor 10, as shown in FIG. 25 with the retractor 10 in the closed position, such that a distal end 204d of the instrument 204 extends through the working channel 20 to access bone, tissue, and/or other matter at the surgical site 202. Although a grasper with jaws is illustrated as the instrument 204 in FIG. 25, a person skilled in the art will appreciate that any instrument can be inserted through the working channel 20.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device, e.g., the blades, can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method for retracting tissue, comprising:
   mating a plurality of protrusions on a first retractor blade directly to a first subset of a first plurality of openings formed through a first portion of a base of a retractor without being mated to a remainder of the first plurality of openings, the first plurality of openings being configured to directly mate to the plurality of protrusions on the first retractor blade such that the protrusions extend all the way through the openings to a side of the base opposite the first retractor blade;
   mating a plurality of protrusions on a second retractor blade directly to a second subset of a second plurality of openings formed through a second portion of the base without being mated to a remainder of the second plurality of openings, the second plurality of openings being configured to directly mate to the plurality of protrusions on the second retractor blade such that the protrusions extend all the way through the openings to a side of the base opposite the second retractor blade; and
   with the first retractor blade directly mated to the first subset of the first plurality of openings and with the second retractor blade directly mated to the second subset of the second plurality of openings, inserting the first and second retractor blades through an incision formed in tissue, and actuating at least one adjustment mechanism on the base to move the first and second retractor blades relative to one another to thereby expand the incision.

2. The method of claim 1, further comprising, prior to inserting, mating a third retractor blade to the base of the retractor, and wherein the first, second, and third retractor blades are inserted through the incision.

3. The method of claim 2, wherein actuating at least one adjustment mechanism comprises actuating a first adjustment mechanism to move the first and second retractor blades relative to one another, and actuating a second adjustment mechanism to move the third retractor blade relative to the first and second retractor blades.

4. The method of claim 2, wherein the first and second retractor blades move simultaneously, and the third retractor blade is movable independent of the first and second retractor blades.

5. The method of claim 2, wherein the first and second retractor blades mate to a distal surface of the base, and the third retractor blade mates to a proximal surface of the base.

6. The method of claim 1, further comprising detaching the first retractor blade from the first subset of the first plurality of openings on the first portion of the base and directly mating the first retractor blade to a different subset of the first plurality of openings on the first portion of the base.

7. The method of claim 1, wherein each of the first and second retractor blades is mated to the base by a compression fit.

8. The method of claim 1, wherein each of the first and second retractor blades have a corrugated cross-sectional shape.

9. The method of claim 1, wherein the first and second retractor blades are mated to a distal facing surface of the base.

10. The method of claim 1, further comprising, after expanding the incision, radioimaging an area including the incision to produce a radio image, the base and the retractor blades mated to the base being radiolucent such that the base and the retractor blades mated to the base are not visible in the radio image.

* * * * *